(12) United States Patent
Raissi

(10) Patent No.: US 10,379,083 B2
(45) Date of Patent: Aug. 13, 2019

(54) ELECTRONIC DEVICE FOR DETECTION OF VIRUSES, BACTERIA, AND PATHOGENS

(71) Applicant: Farshid Raissi, Tehran (IR)

(72) Inventor: Farshid Raissi, Tehran (IR)

( * ) Notice: Subject to any disclaimer, the term of this patent is extended or adjusted under 35 U.S.C. 154(b) by 96 days.

(21) Appl. No.: 15/398,644

(22) Filed: Jan. 4, 2017

(65) Prior Publication Data

US 2017/0115252 A1 Apr. 27, 2017

(51) Int. Cl.
*G01N 27/92* (2006.01)
*G01N 35/00* (2006.01)
*G01N 33/487* (2006.01)

(52) U.S. Cl.
CPC ....... *G01N 27/92* (2013.01); *G01N 33/48707* (2013.01)

(58) Field of Classification Search
CPC ......... G01N 27/00; G01N 25/18; G01N 27/92
USPC ........................ 422/68.1, 82.01; 436/43, 149
See application file for complete search history.

(56) References Cited

U.S. PATENT DOCUMENTS

| | | | | |
|---|---|---|---|---|
| 5,594,263 | A * | 1/1997 | Bedard | .............. H01L 51/4233 257/201 |
| 5,957,858 | A | 9/1999 | Micheels et al. | |
| 8,981,298 | B2 | 3/2015 | Wagner et al. | |
| 9,103,775 | B2 | 8/2015 | Bradley et al. | |
| 9,267,919 | B1 * | 2/2016 | Larkins | ................. G01N 27/49 |
| 9,488,648 | B2 | 11/2016 | Neely et al. | |
| 2007/0210349 | A1 * | 9/2007 | Lu | ............................. B72Y 5/00 257/252 |
| 2014/0030627 | A1 * | 1/2014 | Gidwani | ................. H01M 8/10 429/479 |
| 2017/0170025 | A1 * | 6/2017 | Dahal | ................. H01L 21/3063 |
| 2018/0277530 | A1 * | 9/2018 | Or-Bach | ................. H01L 25/50 |

\* cited by examiner

*Primary Examiner* — Brian J. Sines
(74) *Attorney, Agent, or Firm* — NovoTechIP International PLLC

(57) ABSTRACT

This invention relates to identification of organic or nonorganic molecules dissolved in liquid solutions based on their internal dipole moment. These molecules include and are not limited to viruses, microbes, bacteria, and in general pathogens. The liquid solution provides a specific dielectric constant, which is directly related to the internal dipole moment of the dissolved pathogen. An electronic device namely PtSi-Porous Si schottky junction is proposed as the pathogen detector. This device, which is made of PtSi alloy covering the pores of an n-type Silicon substrate, is a sensitive indicator of the dielectric constant of the material filling its pores. In particular, such a device has a unique reverse biased current-voltage (IV) relation that is sensitive to changes in electric fields around its surface, which change its breakdown voltage. The change caused in the breakdown voltage due to a pathogen dissolved in a liquid solution can be traced back to the dipole moment of the pathogen and used to identify it. Furthermore, application of a frequency varying ac signal to the device can help distinguish molecules with identical dipole moments. Each pathogen exhibits a frequency at which a sudden change in its characteristics occurs. This change in the characteristics causes an abrupt change in the breakdown voltage. The frequency at which the breakdown voltage changes is then used to identify the pathogen.

6 Claims, 4 Drawing Sheets

ELECTRONIC DEVICE FOR DETECTION OF VIRUSES, BACTERIA, AND PATHOGENS

CROSS REFERENCE TO RELATED APPLICATION

This application claims the benefit of priority to an Iran patent application having serial number 139450140003011299 filed on Jan. 4, 2016, which is incorporated by reference herein in its entirety.

TECHNICAL FIELD

The present application relates generally to an electronic device for detection of viruses, bacteria, and pathogens, and more particularly, to a metal-porous semiconductor schottky junction as a detector of viruses, bacteria, and pathogens.

BACKGROUND

Identification and classification of pathogens is a subject of considerable research and commercial interest. A major portion of a discipline called microfluidics is dedicated to such purposes. Microfluidics takes advantage of general and specific fluid dynamics in micrometer and nanometer-sized channels and paths to segregate and possibly identify certain pathogens. Though in its infancy, microfluidics has had a large impact in diagnostics of disease, DNA analysis and the like.

In microfluidics, a network of micrometer or nanometer-sized channels are created and used for identifying pathogens. These networks provide channels of different diameters with a number of outlet and inlet ports that can segregate particular pathogens. After separating the pathogens, a combination of optical, mechanical and chemical diagnostics can be used to identify the material under test.

In the past, micrometer or nanometer-sized channels have been created on Si, glass and polymers surfaces. Although the use of these surfaces has helped in identifying certain pathogens, a need exists for a solution for providing fast, easy, cost effective and accurate identification of pathogens.

SUMMARY

The instant application describes an electronic device for identifying molecules. The electronic device includes a metal semiconductor schottky contact having a porous surface, where the porous surface is comprised of a plurality of sharp edges. The electric field at one or more of the plurality of sharp edges is affected by one or more types of molecules in a material poured on the porous surface and the effect on the electric field causes a change in a breakdown voltage of the electronic device.

The application also describes a method of identifying molecules using an electronic device. The method includes pouring a material having one or more types of molecules over a surface of a metal semiconductor schottky contact having a porous surface, measuring a breakdown voltage of the electronic device, and identifying at least one of the one or more types of molecules based on the measured breakdown voltage.

BRIEF DESCRIPTION OF THE DRAWINGS

Features of the subject technology are set forth in the appended claims. However, for purpose of explanation, several implementations of the subject technology are set forth in the following figures.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings. As part of the description, some of this disclosure's drawings represent structures and devices in block diagram form in order to avoid obscuring the invention. In the interest of clarity, not all features of an actual implementation are described in this specification. Moreover, the language used in this disclosure has been principally selected for readability and instructional purposes, and may not have been selected to delineate or circumscribe the inventive subject matter, resort to the claims being necessary to determine such inventive subject matter. Reference in this disclosure to "one embodiment" or to "an embodiment" means that a particular feature, structure, or characteristic described in connection with the embodiment is included in at least one embodiment of the invention, and multiple references to "one embodiment" or "an embodiment" should not be understood as necessarily all referring to the same embodiment.

Figure 1B:
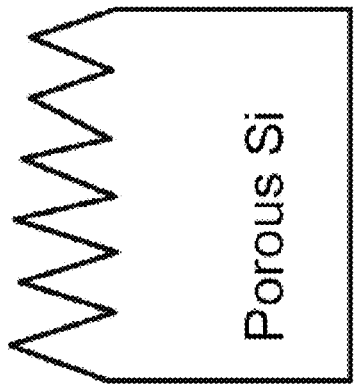
FIG. 1B illustrates a schematic drawing of the side view of a Silicon wafer device having a porous surface, according to an implementation.
Figure 1D:
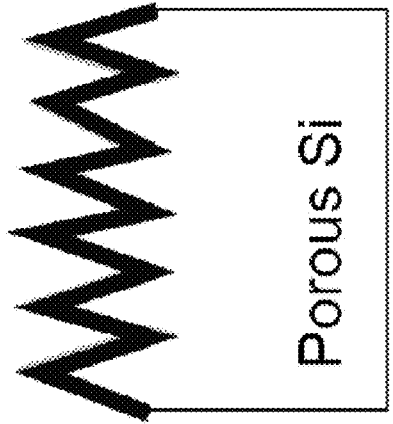
FIG. 1D illustrates a schematic drawing of a PtSi device for identifying one or more types of molecules, according to an implementation.
Figure 1A:
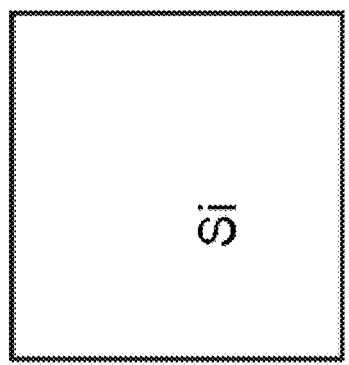
FIG. 1A illustrates a schematic drawing of the side view of a regular Silicon wafer device, according to an implementation.

Being able to accurately and cost effectively identify pathogens is a highly important task in the healthcare industry. In the field of microfluidics, Silicon (Si) has been used in some cases, to identify pathogens. Porous Si has also been utilized in portions of the lab-on-chip devices. One advantage of porous Si is that it provides a very large area for placement and ultimately identification of pathogens. In some devices, which operate based on adhesion of material to the substrate, this larger area provides a higher probability of adhesion and subsequent detection. FIGS. 1A and 1B illustrate the differences in shape between two devices having Si and porous Si surfaces. FIG. 1A depicts a side view of a regular Silicon wafer and FIG. 1B shows the side view of a Silicon wafer for which the top surface has been made porous. The porous surface is represented by a saw tooth surface. As can be seen, because of the top porous surface, porous Si has a larger surface for placement and adhesion of materials.

Figure 1C:
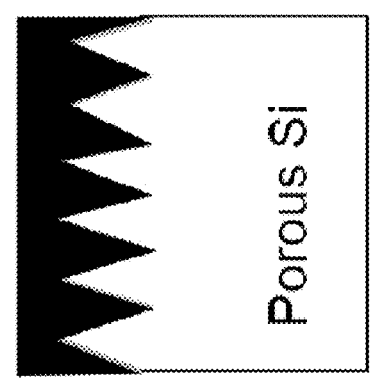
FIG. 1C illustrates a schematic drawing of the side view of the Silicon wafer of FIG. 1B having Pt, according to an implementation.

To improve on advantageous characteristics of the use of porous Si, the preferred embodiment of this disclosure makes use of Si in conjunction with the alloy PtSi. This is illustrated in FIGS. 1C-1D. FIG. 1C shows a Silicon wafer having Pt fill its pores completely, while FIG. 1D illustrates a Silicon wafer on which Pt has been annealed and a PtSi layer has been grown onto the walls of its pores. The remaining Pt has been etched away and removed. The Silicon wafer shown in FIG. 1D consists of porous Si with PtSi covering all its walls. Thus, PtSi covered the porous surfaces of the device shown in FIG. 1D and create a metal contact to Si. Due to their chemical potential difference, Si and PtSi create a schottky junction.

Figure 2A:
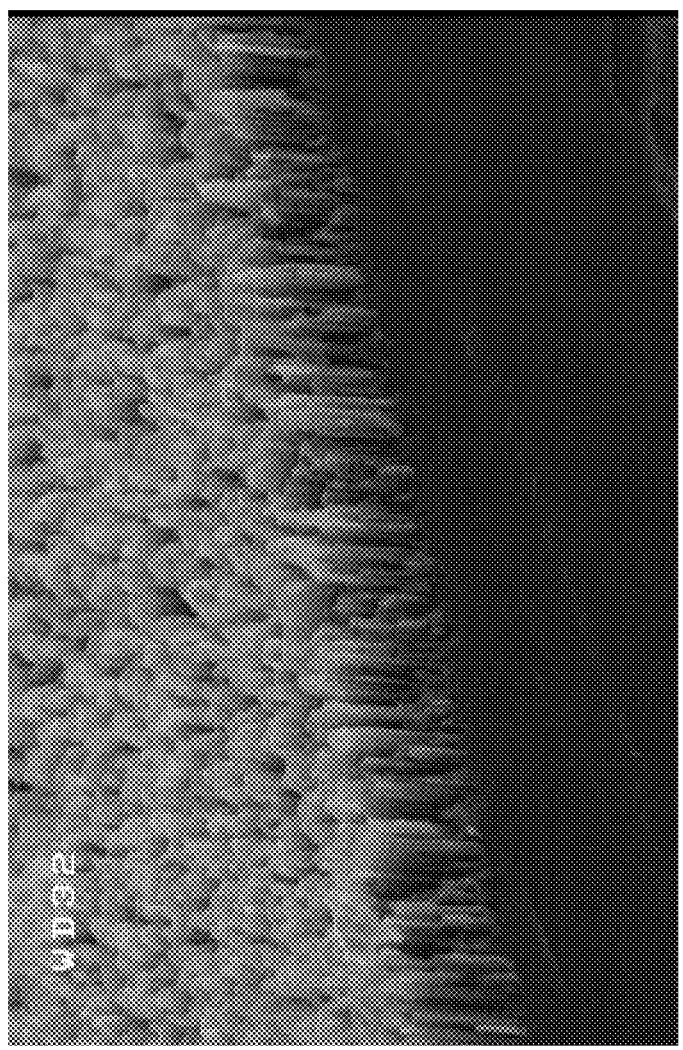
FIGS. 2A-2B illustrate scanning electron microscope (SEM) microphraphs of a metal-porous semiconductor schottky junction, according to an implementation.
Figure 2B:
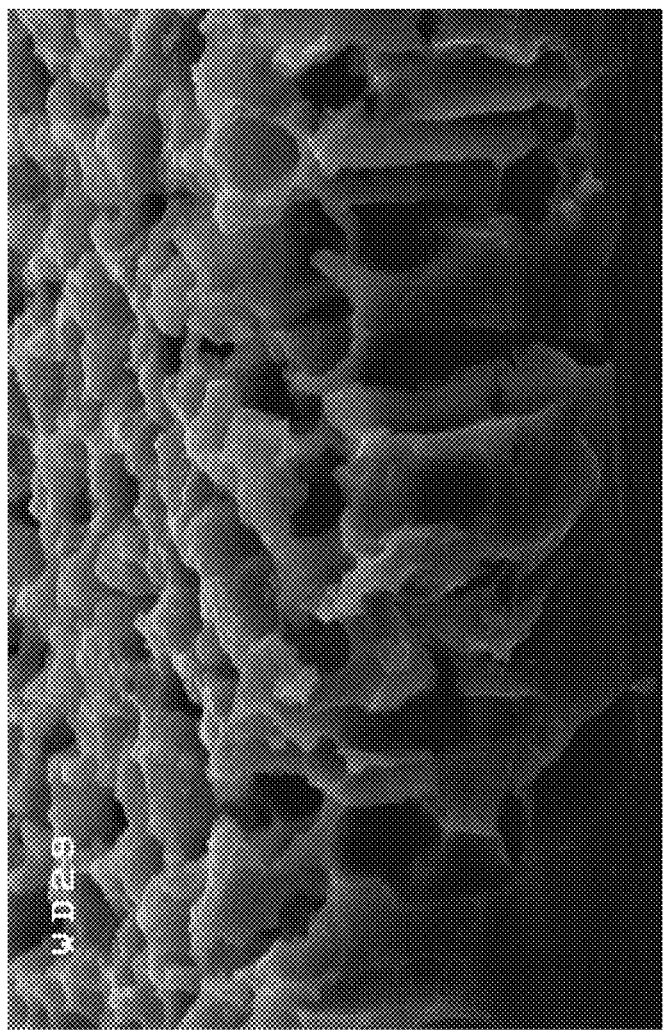

Schottky junction is an electronic device created by connecting a metal with a semiconductor. FIGS. 2A-2B illustrate SEM micrographs of the surface of a PtSi semiconductor schottky junction. FIG. 2A shows the side view SEM micrograph of a cleaved porous wafer. The bottom silicon layer is black in this figure and the spongy white areas are where PtSi has covered the sidewalls of the pores. FIG. 2B is the SEM micrograph of the same wafer as shown in FIG. 2A with a higher resolution clearly showing the holes and crevices of the porous surface over whose walls PtSi has created the white color.

In general, a Schottky junction device provides a nonlinear current-voltage (I-V) relation, which is rectifying with respect to current direction. As such, the schottky junction allows current to pass at one voltage polarity and impedes it in the other. The voltage polarity in which current is blocked is known as the reverse bias mode. Metals and alloys other than PtSi can also create schottky contacts and can be used in the detection of pathogens. Thus, alternative embodiments of the present disclosure make use of such other metals and alloys. However, PtSi is preferable in one embodiment, due to reproducibility of junction characteristics and lack of problems with surface states at the metal-semiconductor junction. In particular, the reverse bias mode of the porous PtSi semiconductor schottky junction exhibits characteristics, which are optimal for detection purposes. Some of these characteristics are in part attributed to single-electron phenomenon and avalanche breakdown multiplication occurring in the reverse bias mode of the porous semiconductor schottky junction.

In general, regular schottky junctions are not very sensitive to the dielectric constant of the surrounding environment. However, a schottky junction made of PtSi over the surface of porous Si adds a new physical phenomenon known as the single-electron effect to the behavior of the junction, making it very sensitive to the surrounding environment. The reverse bias I-V is characterized by a breakdown voltage, after which current increases in a cliff-like fashion. The breakdown voltage is, generally, a direct result of the electric fields developed at the sharp edges of the pores. In general, the electric fields at the sharp edges and tips of irregular porous surfaces are orders of magnitude larger than the electric fields at the sharp edges and tips of surfaces of regular junctions. These very large electric fields are important factors for the occurrence of breakdown voltage as well as single-electron effect in porous samples. Single-electron effect keeps the current small and below the level of causing breakdown voltage despite the very large area the porous surface provides. Breakdown voltage creates the means by which the surrounding material can be easily distinguished electrically.

Figures 3A, 3B, 3C:
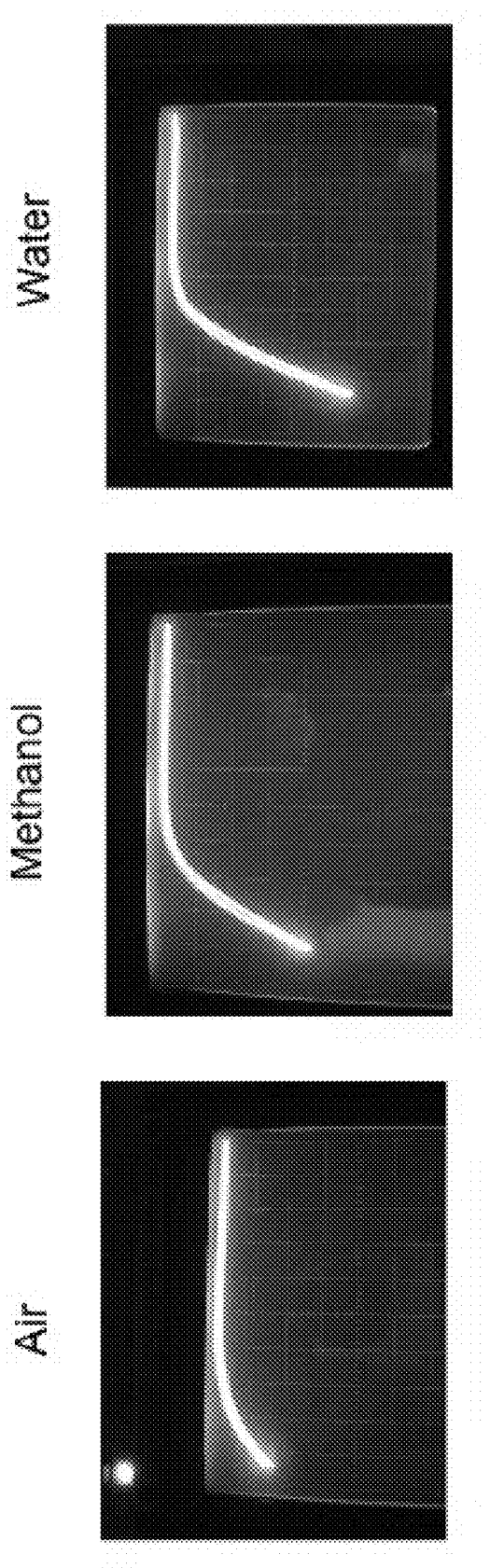
FIGS. 3A-3C illustrate I-V curve graphs and their changes with different materials in the pores of a metal-porous semiconductor schottky junction, according to an implementation.

Anything that affects distribution or magnitude of the electric fields at the sharp edges and tips of the surfaces can change breakdown voltage of the device. For example, experiments have shown that the preferred embodiment of the porous semiconductor schottky junction of this disclosure is sensitive to ambient gas filling its pores. This means that ambient gas affects the distribution and/or magnitude of the electric fields of the surface of the porous semiconductor schottky junction, thus changing the breakdown voltage of the device. This can be used to distinguish between gases with different electrical dipole moments. This is illustrated in FIGS. 3A-3C. These figures show I-C curves of a porous semiconductor schottky junction with different materials in its pores. FIG. 3A shows the I-C curve of the porous semiconductor schottky junction with just air (i.e. no material or solution poured on the surface). FIG. 3B shows the I-C curve with methanol on its' surface and FIG. 3C illustrates the I-C curve with water poured on the pores of the porous semiconductor schottky junction. As can be seen the I-C curves are very different for each of these materials, and the breakdown voltage (the point at which the current increases in a cliff-like fashion) has a different value in each graph.

The preferred embodiment of the disclosed porous semiconductor schottky junction can also be used to identify liquid solutions, and in particular liquids containing different pathogens. In one embodiment, a liquid under test is poured over the surface of the device. In general, some liquids get inside the pores and wet the whole surface, while some liquids do not. In order for all liquid types to get into the pores, in one embodiment, a predetermined proper polarity of voltage is applied to the junction's surface. By applying the proper polarity, the liquid types that do not normally enter the pores can be made to get into the crevices and wet the entire surface. Some materials are made to enter the pores with positive bias and some with negative bias. Since the schottky junction is to be biased in its reverse bias mode, depending on the material (solution) in question either n or p type semiconductor can be used, such that the reverse bias polarity corresponds to the polarity for which the solution is attracted into the pores. For liquid solutions that enter the pores with positive voltage, a p type semiconductor is used so that its reverse bias mode provides a positively biased surface to the liquid. In contrast, for liquid solutions that need a negative voltage to enter the pores, an n type semiconductor is used.

The change in the breakdown voltage is different for different liquid solutions. Because of this difference, the process of identifying the types of molecules in the solution can be fast and reproducible. For example, the breakdown voltage of each known virus, bacteria or microbe can be measured and recorded using a porous semiconductor schottky junction. Afterwards, the relative change in breakdown voltage caused by an unknown pathogen can be compared to the recorded values to identify the corresponding pathogen. In one embodiment, to obtain better selectivity or sensitivity, a pathogen can be dissolved in different liquid solutions.

The change in the breakdown voltage is, generally, a function of both the concentration and the dipole moment of the material dissolved in the liquid solution. To segregate these factors out, in one embodiment of this disclosure, an alternative voltage (i.e., ac voltage) is superimposed on the dc reverse bias voltage. In general, each organic molecule has a characteristic frequency at which it changes the IV curve. In other words, as the frequency of the ac signals is swept up to mega Hertz regime, at a certain frequency, there is a change in threshold voltage. This change does not depend on the concentration and only depends on the molecule itself. The type of changes that take place in the molecule itself at its characteristic frequency re not yet completely known, but it is clear that such a change happens at a different frequency for each different molecule. It should be noted that even if the solvent is made of several types of molecules, the change in the threshold voltage happens at every frequency that each type of molecule is susceptible to. In other words, there is no limit to the number of types of molecules that can be dissolved in the solvent and all the different types of molecule constituents can be identified independently. That is the case if the different types of molecules do not recombine to create a new one.

Different types of molecules have different sizes. For example, some molecules may be very long or very short. Because of the difference in size of molecules, some pore sizes may not allow a number of molecules to enter them. That is they may only allow certain types of molecules inside keeping the rest out. As a result, in one embodiment, the size, depth, and density of the pores of the surface of the porous semiconductor schottky junction is tailored for initial segregation of organic molecules. In effect, in one embodiment of the present disclosure, different porosity levels are used for the porous semiconductor schottky junction as filters or attractors of molecules.

In another embodiment, a variety of materials that are known to cause chemical reaction with certain pathogens can be added to the liquid solution before a liquid solution is poured over the surface of the porous semiconductor schottky junction. This is because chemical reaction changes the molecule's formula and a change in threshold voltage is thus detected.

One or all the above methods or any other procedures that change the chemical or physical properties of a molecule or a combination of molecules can be used to discriminate and identify pathogens or organic materials under investigation by the changes it induces in the threshold voltage of the porous semiconductor schottky junction.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus the following claims are hereby incorporated into the Detailed Description, with each claim standing on its own as a separately claimed subject matter.

What is claimed is:

1. A method of identifying molecules using an electronic device comprising:
    pouring a material having one or more types of molecules over a surface of a metal semiconductor schottky contact having a porous surface;
    measuring a breakdown voltage of the electronic device; and
    identifying at least one of the one or more types of molecules based on the measured breakdown voltage,
    wherein at least one of a size, depth, and density of the plurality of sharp edges segregates the one or more types of molecules.

2. The method of claim 1, wherein the porous surface is comprised of a plurality of sharp edges, an electric field at one or more of the plurality of sharp edges is affected by the at least one type of molecule in the material poured on the porous surface; and the effect on the electric field at one or more of the plurality of sharp edges causes a change in the breakdown voltage of the electronic device.

3. The method of claim 1, wherein the measured breakdown voltage is compared to one or more known breakdown voltage values to identify the at least one of the one or more types of molecules.

4. The method of claim 1, further comprising applying a predetermined proper polarity of voltage to the porous surface after the material has been poured on the porous surface.

5. The method of claim 3, wherein the predetermined proper polarity is at least one of a negative bias or a positive bias and is selected based on a type of the material.

6. The method of claim 1, further comprising applying ac signals of different frequencies to the porous surface after the material has been poured on the porous surface to cause a change in one or more properties of the one or more types of molecules.

* * * * *